United States Patent [19]

Schloemer et al.

[11] Patent Number: 5,567,816

[45] Date of Patent: Oct. 22, 1996

[54] PREPARATION OF ACYCLOVIR USING 1,3 DIOXOLANE

[75] Inventors: George C. Schloemer, Longmont; Yeun-Kwei Han; Peter J. Harrington, both of Louisville, all of Colo.

[73] Assignee: Syntex (U.S.A.) Inc., Palo Alto, Calif.

[21] Appl. No.: 426,005

[22] Filed: Apr. 27, 1995

Related U.S. Application Data

[63] Continuation-in-part of Ser. No. 280,269, Jul. 26, 1994, abandoned.

[51] Int. Cl.$^6$ ................................................. C07D 473/18
[52] U.S. Cl. ............................................................. 544/276
[58] Field of Search ................................................. 544/276

[56] References Cited

U.S. PATENT DOCUMENTS 4,360,522   11/1982   Schaeffer et al. ........................ 424/253
4,803,272   2/1989   Anton et al. ............................. 544/277

FOREIGN PATENT DOCUMENTS 0072027   2/1983   European Pat. Off. .
532878   3/1993   European Pat. Off. .
5-213903   8/1993   Japan .

OTHER PUBLICATIONS

Partial Abstract for JP 62–151189 (1986).
M. M. Mansuri et al., "1–(2–Deoxy–2–fluoro–β–D–arabinofuranosyl)–5–ethyluracil. A Highly Selective Antiherpes Agent", *J. Med. Chem.*, 30(5), pp. 867–871 (1987).
W. T. Ashton et al., "Synthesis and Antiherpetic Activity of (S)–, (R)–, and (±)–9–[2,3–Dihydroxy–1–propoxy)methyl] guanine, Linear Isomers of 2'–Nor–2'–deoxyguanosine", *J. Med. Chem.*, 28(7), pp. 926–933 (1985).
M. Madre et al., "Analogs of Purine Nucleosides. I. Methods for Synthesis of 9–(2–hydroxyethoxymethyl)guanine–Acycloguanosine", *Khim.–Farm. Zh.*, 19(11), pp. 1371–1375 (1985).
S. V. Kochetkova et al., "Simple and Convenient Method for the Synthesis of Guanosine Acyclic Analogs", *Bioorg. Khim.*, 15(1), pp. 133–135 (1989).
I. P. Smirnov et al., "Compounds Related to Acyclovir. III. Synthesis of Analogs of 5'–Deoxynucleosides", *Bioorg. Khim.*, 14(7), pp. 921–925 (1988).
I. P. Smirnov et al., "Compounds Related to Acyclovir. VI. Synthesis of OPtically Active 1',2'–Seconucleosides", *Bioorg. Khim.*, 16(10), pp. 1355–1361 (1988).
J. Kjellberg et al., *Nucleosides & Nucleotides*, 8(2), pp. 225–256 (1989).
*Zhongguo Yaoke Daxue Zuebao*, 23(1), pp. 43–44 (1992).
F. P. Clausen et al., *Org. Prep. Proced. Int.*, 25(4), pp. 375–401 (1993).
H. Matsumoto et al., *Chem. Pharm. Bull.*, 36(3), pp. 1153–1157 (1988).

*Primary Examiner*—Mark L. Berch
*Attorney, Agent, or Firm*—Heller Ehrman White & McAuliffe

[57] ABSTRACT

A process for the preparation of acyclovir includes contacting an at least partially silylated guanine or mixture of at least partially silylated guanines with 1,3-dioxolane in the presence of a selective alkylation catalyst selected from the group consisting of trifluoromethanesulfonic acid, trimethylsilyl trifluoromethanesulfonate, and bistrimethylsilyl sulfonate, and hydrolyzing the product thus formed.

25 Claims, No Drawings

PREPARATION OF ACYCLOVIR USING 1,3 DIOXOLANE

This is a Continuation-in-Part of U.S. patent application Ser. No. 08/280,269, filed Jul. 26, 1994, now abandoned the complete disclosure of which is hereby incorporated by reference.

BACKGROUND OF THE INVENTION

1. Field of the Invention

The present invention relates to a process for the synthesis of acyclovir.

2. Background Information and Related Disclosures

Many synthetic N-substituted derivatives of purines and related nucleosides have been shown to exhibit significant antiviral properties. One notable example is the N-9 alkylated product 9-(2-hydroxyethoxymethyl)guanine, (i.e. acyclovir). It is clearly desirable to have inexpensive and efficient processes for manufacturing such a compound.

The usefulness of any process for manufacturing chemical compounds is gauged by several factors. For example, starting materials should be as simple structurally as feasible (so as to keep their costs low). The process is more efficient if intermediates do not require isolation and/or purification, since these procedures result in additional steps and lower yield. The process should yield a product that is free of byproducts (e.g., undesired isomers and/or chemical reagents). Shortcomings in any of the above parameters result in increased manufacturing costs, which impacts negatively on the desirability of the process.

The simplest synthetic approach to the N-9 substituted guanine compounds involves direct alkylation of a protected guanine base. However, there are significant drawbacks to this approach. In many reported processes, guanine protected by acyl groups (for example, diacetylguanine) is employed as the protected guanine base. However, acyl groups prove difficult to remove at the completion of the process, resulting in lower yields. Also, known alkylation processes are not regiospecific for the N-9 position of the protected guanine base, and result in a mixture of N-9 and N-7 alkylation products. The undesired N-7 isomer is difficult to separate from the desired N-9 isomer, requiring chromatography for isolation. Chromatographic separation on a commercial scale is most undesirable, because of the increased costs associated with such a separation (cost of solvents and stationary phase, low yields of desired product, etc).

Surprisingly, an efficient and selective process has been discovered for preparing the substituted guanine compound acyclovir. The process avoids the use of acyl groups for protection of guanine, is essentially specific for the preparation of the N-9 isomer (thus eliminating the need for the chromatographic separation of the N-9/N-7 isomer mixture), provides good yields, requires simple starting materials and reaction conditions, and is carried out from start to finish in a single reaction vessel.

One important aspect of the invention relates to the choice of the acid catalyst, which is critical to the success of the process. Use of common acid catalysts such as sulfuric acid, methanesulfonic acid, p-toluenesulfonic acid, and the like, gives low yields and undesired byproducts. Only certain selective alkylation catalysts give high yields and highly selective N-9 alkylation.

Previous processes for the preparation of acyclovir and similar compounds are disclosed in U.S. Pat. Nos. 4,355, 032, 4,360,522, 4,621,140, and 5,250,535, European Patent Applications 152,965, 532,878, and 72,027, and JP 5213903. Syntheses of related compounds are disclosed in *Nucleosides Nucleotides*, 8(2), pp 255–256 (1989), *Zhongguo Yaoke Daxue Xuebao*, 23(1), pp 43–44 (1992), *Org. Prep. Proced. Int*, 25(4), pp 375–401 (1993), *J. Med. Chem.*, 26(5), 759–61 (1983), *Synth. Commun.*, 18(14), 1651–60 (1988), and *Chem. Pharm. Bull.*, 36(3), 1153–1157 (1988).

SUMMARY OF THE INVENTION

The invention relates to an efficient and selective process for preparing a compound represented by the formula:

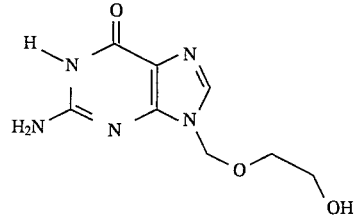

said process comprising:

a) contacting guanine with a silylating agent to give a compound or mixture of compounds represented by the formula:

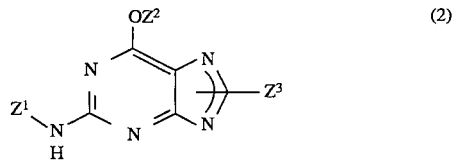

wherein:

$Z^1$ is hydrogen or $R^1R^2R^3Si$;

$Z^2$ is hydrogen or $R^1R^2R^3Si$;

$Z^3$ is hydrogen or $R^1R^2R^3Si$;

in which $R^1$, $R^2$, and $R^3$ are independently lower alkyl; provided that at least one of $Z^1$, $Z^2$, and $Z^3$ is $R^1R^2R^3Si$; followed by:

b) contacting the protected guanine or mixture of protected guanines thus formed, represented by Formula (2), with a compound of the formula:

i.e. 1,3-dioxolane; in the presence of a selective alkylation catalyst, and c) hydrolyzing the product thus formed.

Alternatively, the intermediate formed by condensation of the protected guanine of Formula (2) with a compound of Formula (3) in the presence of a selective alkylation catalyst, i.e. a compound represented by the formula:

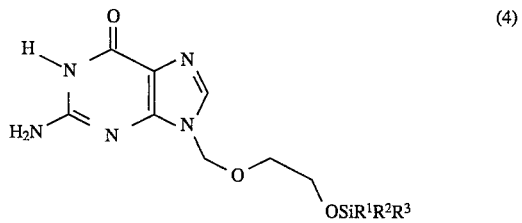

where $R^1$, $R^2$, and $R^3$ areas defined above; is (b) isolated as a solid by precipitation or crystallization from an inert solvent; and c) the purified compound of Formula (4) is then hydrolyzed.

DETAILED DESCRIPTION OF THE INVENTION

Definitions and General Parameters

The following definitions are set forth to illustrate and define the meaning and scope of the various terms used to describe the invention herein.

The term "lower alkyl" means a monoradical branched or unbranched saturated hydrocarbon chain containing 1 to 6 carbon atoms, such as methyl, ethyl, n-propyl, isopropyl, n-butyl, tert-butyl, n-pentyl, n-hexyl, and the like, unless otherwise indicated.

The term "alkanoic acid" means a monobasic carboxylic acid derived from lower alkyl as defined above, such as formic acid, acetic acid, propionic acid, n-butyric acid, isobutyric acid, n-valeric acid, isovaleric acid, trimethylacetic acid, caproic acid, and the like, unless otherwise indicated.

The term "silylation catalyst"0 refers to catalysts such as ammonium sulfate, p-toluenesulfonic acid, trifluoromethanesulfonic acid, trimethylsilyl trifluoromethanesulfonate, bistrimethylsilyl sulfonate, sulfuric acid, potassium butylsulfonate, ammonium perchlorate, sodium perchlorate, sodium borofluoride, tin tetrachloride, and the like.

The term "selective alkylation catalyst" refers to catalysts such as trimethylsilyl perchlorate, trifluoromethanesulfonic acid, trimethylsilyl trifluoromethanesulfonate, and bistrimethylsilyl sulfonate.

The terms "inert organic solvent" or "inert solvent" mean a solvent inert under the conditions of the reaction being described in conjunction therewith [including, for example, benzene, toluene, acetonitrile, tetrahydrofuran ("THF") dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, water, and the like]. Unless specified to the contrary, the solvents used in the reactions of the present invention are inert solvents.

The term "hydrolyzing" or "hydrolysis" refers to the process of splitting a chemical bond by the addition of water; for example, hydrolysis of an alkyl ester gives an organic acid and an alcohol, hydrolysis of an amide gives an organic acid and an amine, hydrolysis of a silyl ether gives an alcohol. Hydrolysis may be accomplished by treatment with an inorganic acid, for example hydrochloric acid, or an organic acid, for example acetic acid, or by treatment with a base, for example sodium hydroxide or ammonium hydroxide.

"Optional" or "optionally" means that the subsequently described event or circumstance may or may not occur, and that the description includes instances where said event or circumstance occurs and instances in which it does not.

The term "silylating agent" as used herein refers to a compound capable of silylating guanine. A preferred silylating agent is hexamethyldisilazane (which will give a compound of Formula (2) where at least one Z is a silyl group of formula SiR$^1$R$^2$R$^3$, in which R$^1$, R$^2$, and R$^3$ are all methyl). However, many other silylating agents are known in the art. For example, guanine may be reacted with a trialkylsilyl halide of formula SiR$^1$R$^2$R$^3$X, in which R$^1$, R$^2$, and R$^3$ are independently lower alkyl and X is chloro or bromo, such as trimethylsilyl chloride, tert-butyldimethylsilyl chloride, and the like, preferably in the presence of about 1–2 molar equivalents of a base.

The compound of Formula (2) is represented as follows:

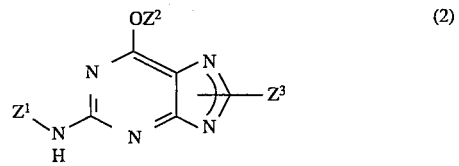

(2)

Formula (2) represents guanine protected by one, two, or three silyl groups, or a mixture thereof, where Z$^1$, Z$^2$, and Z$^3$ are independently hydrogen or a silyl group of formula SiR$^1$R$^2$R$^3$, provided that at least one of Z$^1$, Z$^2$, and Z$^3$ must be a silyl group, in which R$^1$, R$^2$, and R$^3$ are independently lower alkyl. It should be noted that Formula (2) as drawn represents a mixture of N-7 and N-9 isomers (as a tautomeric mixture).

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples hereinbelow. However, other equivalent separation or isolation procedures can also be used.

Nomenclature

The following numbering and nomenclature system will be used for describing and naming the compounds of the invention.

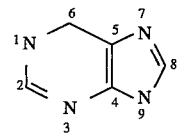

Thus, the compound of Formula I is named 9-(2-hydroxyethoxymethyl)guanine, i.e., acyclovir.

SUMMARY OF THE PROCESS FOR PREPARING A COMPOUND OF FORMULA I

The process for the preparation of the compound of Formula I is shown below in Reaction Scheme A.

REACTION SCHEME A

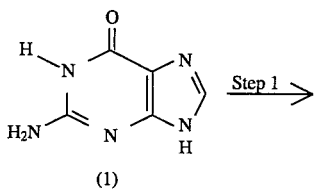

(1)

-continued
REACTION SCHEME A

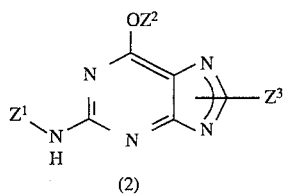

(2)

where $Z^1$, $Z^2$ and $Z^3$ are independently hydrogen or a silyl protecting group of the formula $R^1R^2R^3Si$, in which $R^1$, $R^2$, and $R^3$ are independently lower alkyl, provided that at least one of $Z^1$, $Z^2$ and $Z^3$ is a silyl group;

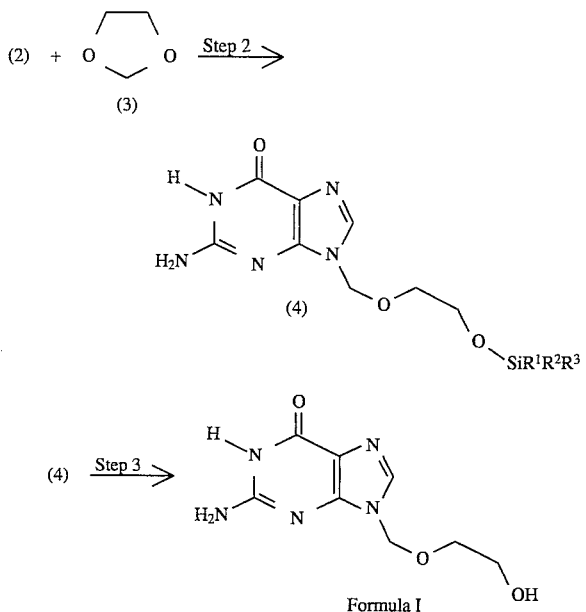

Formula I

Starting Materials

The trialkylsilyl halides of formula $R^1R^2R^3SiX$ (where X is chloro or bromo), hexamethyldisilazane, and the compounds of Formula (1) and (3), are all commercially available.

Step 1: Preparation of Formula (2)

As illustrated in Reaction Scheme A, in the first step guanine (Formula (1)) is silylated to give the corresponding protected guanine.

The protection of guanine prior to alkylation is well known in the art (see, for example "Synthesis of 9-substituted Guanines. A Review" by F. P. Clausen and J. J. Christensen *Org. Prep. Proced. Int,* 25(4), pp 375–401 (1993)). Guanine may be, for example, be protected using acyl groups, for example acetyl, or by silyl groups. Traditionally, when silyl groups are employed for protection, guanine is silylated in such a manner that all active protons present in guanine are replaced by a silyl group before proceeding with the desired reaction, i.e. guanine is protected as the trisilyl derivative. However, surprisingly it has now been discovered that, although trisilylation of guanine followed by the alkylation of Step 2 gives the desired product in good yield, and indeed is preferred, it is not essential that guanine be trisilylated for the alkylation carried out in Step 2 to be essentially specific for the preparation of the N-9 isomer. Conventionally, guanine as a slurry is reacted with a silylating agent, for example hexamethyldisilazane, at reflux until all suspended material goes into solution, which signals the complete formation of the trisilyl derivative. This reaction can take up to 48 hours or more. Surprisingly, it has now been found that refluxing for much less time, for example as little as 2 hours, then reacting the slurry thus produced with 1,3-dioxolane as described in Step 2 below, gives good yields of desired product. Although the composition of a compound of Formula (2) produced by reacting guanine with hexamethyldisilazane for a shortened period of time is not yet known with any certainty, it is believed to be mainly a monosilyl derivative, probably mixed with some disilyl and trisilyl guanine.

In a preferred method, guanine is reacted with about 3–10 molar equivalents of a silylating agent, preferably with hexamethyldisilazane (i.e. to give a compound of formula (2) where $Z^1$, $Z^2$, and $Z^3$ are all silyl groups in which $R^1$, $R^2$, and $R^3$ are methyl), in the presence of a silylating catalyst, preferably ammonium sulfate, trifluoromethanesulfonic acid, trimethylsilyl trifluoromethanesulfonate, or bistrimethylsilyl sulfonate, most preferably trifluoromethanesulfonic acid (about 0.01 to 0.1 molar equivalents). The mixture is heated to reflux over a period of about 5–48 hours, preferably about 16 hours. When the reaction is substantially complete, optionally excess silylating agent is removed under reduced pressure, and the resultant solution of the protected guanine product of Formula (2) is used in the next step without further purification.

Alternatively, guanine is reacted with a silylating agent, preferably hexamethyldisilazane, in the presence of a silylating catalyst, preferably trifluoromethanesulfonic acid, as described in the preceding paragraph but for a period of about 1–8 hours, preferably 2–4 hours. Optionally, excess silylating agent is removed under reduced pressure, and the resultant solution of the protected guanine product of Formula (2) is used in the next step without further purification.

Alternatively, guanine may be reacted with 1–5 molar equivalents of a trialkylsilyl halide of formula $SiR^1R^2R^3X$, in which $R^1$, $R^2$, and $R^3$ are independently lower alkyl and X is chloro or bromo, such as trimethylsilyl chloride, tert-butyldimethylsilyl chloride, and the like, in the presence of about 1–5 molar equivalents of a base.

It should be noted that ammonium sulfate, trifluoromethanesulfonic acid, trimethylsilyl trifluoromethanesulfonate, or bistrimethylsilyl sulfonate work well as acid catalysts in the silylation of guanine described above. However, use of trifluoromethanesulfonic acid is preferred because it is much less expensive than trimethylsilyl trifluoromethanesulfonate or bistrimethylsilyl sulfonate, and is particularly preferred because trifluoromethanesulfonic acid is converted to trimethylsilyl trifluoromethanesulfonate during the course of the silylation reaction, which then functions as the preferred selective alkylation catalyst in Step 2 (i.e. no further catalyst need be added for Step 2).

Step 2: Preparation of Formula (4)

As illustrated in Reaction Scheme A, Step 2, protected guanine (Formula (2)) is selectively alkylated to give the corresponding N-9 isomer of Formula (4), plus a small amount of the N-7 isomer.

To the product of Step 1 is added 1,3-dioxolane (Formula (3)) and about 0.01 to 0.1 molar equivalents of a selective alkylation catalyst (such as trifluoromethanesulfonic acid, trimethylsilyl trifluoromethanesulfonate, or bistrimethylsilyl sulfonate, preferably trimethylsilyl trifluoromethanesulfonate) is added. As noted above, if trifluoromethanesulfonic acid was employed as the catalyst in Step 1, then the preferred trimethylsilyl trifluoromethanesulfonate is formed in situ, and the addition of further selective alkylation catalyst is not necessary.

The reaction mixture is heated to about reflux for a period of about 5 to 24 hours, preferably about 15 hours if no additional solvent is added, or about 10 hours if an inert solvent, preferably toluene, is added to the reaction mixture. Preferably, the compound of Formula (4) thus produced is hydrolyzed as shown in Step 3 below with no further purification. Alternatively, the compound of Formula (4) is purified by precipitation or crystallization from an inert solvent, preferably a mixture of acetone and water.

Step 3: Preparation of Formula (I)

As illustrated in Reaction Scheme A, Step 3, the compound of Formula (4) is hydrolyzed to give the compound of Formula (I).

One method of hydrolysis involves adding to the product of Step 2 an aqueous acid, preferably an alkanoic acid, most preferably aqueous acetic acid, optionally in an inert solvent, for example methanol, toluene, acetone, or mixtures thereof. Preferably a mixture of water and acetic acid is used, the mixture most preferably containing 1–10% of acetic acid. The mixture is heated to about reflux temperature, for about 5–30 minutes, preferably about 10 minutes, in the presence of a decolorizing agent, for example filtrol, then filtered and cooled to a temperature in the range of about 0° to 15° C., preferably about 5° C. Pure compound of Formula (I) is obtained as a crystalline solid.

In a preferred hydrolysis, which eliminates the need for using a decolorizing agent, the product of Step 2 is hydrolyzed with an aqueous base (for example, sodium hydroxide, potassium hydroxide, preferably sodium hydroxide), giving an aqueous solution of a salt of the compound of Formula (I), preferably the sodium salt. This solution is separated and then neutralized (with hydrochloric acid, sulfuric acid, or preferably an alkanoic acid, most preferably acetic acid), resulting in a precipitate of a compound of Formula (I). This precipitate is purified by conventional means, the last step of which entails crystallization from an aqueous ammonium hydroxide solution, which minimizes the amount of bis[9-(2-hydroxyethoxymethyl)guanine]methane produced in the process as a byproduct (see below).

The product of Formula (I) may be purified further by recrystallization from about 15–50 volumes, preferably 20–30 volumes, of water, cooling to about 10°–15° C. Pure compound of Formula (I) is obtained as a crystalline solid.

The compound prepared by the above-described process of the invention may be associated with the presence of a slight but detectable amount of a compound of the formula:

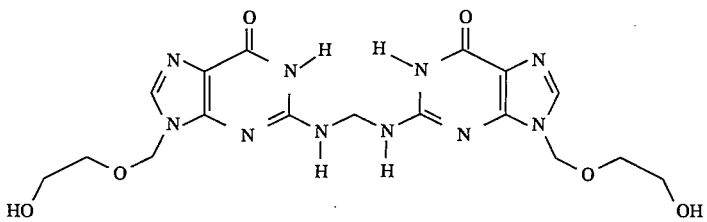

which is named as bis[9-(2-hydroxyethoxymethyl)guanine]methane, produced in the process as a byproduct. Minor amounts of such compounds are detected, for example, using mass spectroscopy, NMR spectroscopy, or preferably analytical HPLC. While it is well known that pharmaceuticals must meet pharmacopoeia standards before approval and/or marketing, and that synthetic reagents or byproducts should not exceed the limits prescribed by pharmacopoeia standards, final compounds prepared by the process of the present invention may have minor, but detectable, amounts of such material present. It is important to monitor the purity of pharmaceutical compounds for the presence of such materials, which presence is additionally disclosed as a method of detecting use of a process of the invention.

PREFERRED PROCESS

A preferred process for the synthesis of acyclovir entails first protecting guanine with trialkylsilyl, preferably trimethylsilyl, most preferably as tris(trimethylsilyl), and reacting this protected compound with 1,3-dioxolane, to give an N-9 substituted guanine of Formula (4) along with a small amount of the N-7 isomer. The reaction is carried out in the presence of a selective alkylation catalyst, preferably trimethylsilyl trifluoromethanesulfonate, and is preferably carried out in the presence of an inert solvent, preferably toluene. The intermediate of Formula (4) thus produced may be purified by precipitation or crystallization from an inert solvent, preferably a mixture of acetone and water, and the purified intermediate then hydrolysed as set forth below. Preferably, the intermediate of Formula (4) is hydrolysed with no intervening purification step, with an aqueous acid, preferably acetic acid, or more preferably with a base, most preferably sodium hydroxide, to give the desired product of Formula (I).

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

Preparation of a Compound of Formula (4)

A mixture of guanine (10 g), hexamethyldisilazane (HMDS, 50 ml), and trifluoromethanesulfonic acid (0.24 ml) was heated to reflux (130°–135° C.) for 16 hours. The resulting mixture was cooled to 35° C., and excess HMDS removed by distillation (0.1 to 1 mm Hg), slowly raising the bath temperature back to 110° C. The mixture was then cooled to below 80° C., 1,3-dioxolane (25 ml) added, and the resulting mixture refluxed for 15 hours. The reaction mixture was cooled to 50° C., and poured into a mixture of acetone (80 ml) and water (8 ml). The resultant slurry was filtered, and the solid material washed with cold acetone, to give 9-(2-trimethylsilylethoxymethyl)guanine (15.8 g, yield 87%).

$^1$H NMR ppm-0.04 (9H, singlet); 3.43 (2H, multiplet); 3.52 (2H, multiplet); 5.27 (2H, singlet); 6.46 (2H, broad singlet); 7.75 (1H, singlet).

The ratio of N-9 to N-7 alkylated product obtained from this reaction typically range from 25:1 to 50:1.

EXAMPLE 2

Preparation of a Compound of Formula (I)

A mixture of 9-(2-trimethylsilylethoxymethyl)guanine (15.8 g), water (250 ml), and acetic acid (20 ml) was heated to reflux, giving a solution. The hot solution was treated with a small amount of Montmorillonite K10 (an acidic clay) to remove any color, filtered, and the filtrate slowly cooled to 5° C. The white crystalline solid thus produced was filtered off, to yield 9-(2-hydroxyethoxymethyl)guanine (8.8 g, 69%). $^1$H NMR 3.38 (4H, singlet); 4.64 (1H, broad singlet); 5.26 (2H, singlet); 6.54 (2H, broad singlet); 7.68 (1H, singlet).

The ratio of N-9 to N-7 alkylated product obtained from this reaction typically range from 1000:1 to 2000:1.

EXAMPLE 3

Alternative Preparation of a Compound of Formula (I)

A mixture of guanine (25 g), hexamethyldisilazane (HMDS, 125 ml), and trimethylsilyl trifluoromethanesulfonate (1 ml) was heated to reflux (130°–135° C.) for 24 hours. The resulting mixture was cooled to 70° C., 1,3-dioxolane (25 ml) added, and the resulting mixture refluxed for 16 hours. Excess HMDS and 1,3-dioxolane were removed by distillation under reduced pressure. The reaction mixture was cooled to 70° C., and poured into a mixture of 600 ml of 10% aqueous acetic acid. The mixture was heated to give a solution. The hot solution was treated with a small amount of activated carbon (1.25 g) to remove any color, filtered, and the filtrate slowly cooled to 5° C. The white crystalline solid thus produced was filtered off, to yield pure 9-(2-hydroxyethoxymethyl)guanine (29 g, 78%). $^1$H NMR: 3.38 (4H, singlet); 4.64 (1H, broad singlet); 5.26 (2H, singlet); 6.54 (2H, broad singlet); 7.68 (1H, singlet).

EXAMPLE 4

Alternative Preparation of a Compound of Formula (I)

A mixture of guanine (25 g), hexamethyldisilazane (HMDS, 125 ml), and trifluoromethanesulfonic acid (0.75 ml) was heated to reflux (130°–135° C.) for 16 hours. The resulting mixture was cooled to 70° C., and excess HMDS removed by distillation (0.1 to 1 mm Hg), slowly raising the bath temperature back to 130° C. The resulting mixture was cooled to 60° C., 1,3-dioxolane (20 ml) added, and the resulting mixture refluxed for 16 hours. The mixture was then cooled to 45° C., 200 ml of methanol added, and then low boiling solvent was removed by distillation at atmospheric pressure. The reaction mixture was cooled, and poured into a mixture of 500 ml water and 10 ml of acetic acid. The mixture was heated to 80° C., removing low boiling material, to give a solution. The hot solution was treated with a small amount of activated carbon (2.5 g) to remove any color, and 100 ml of water added. The slurry thus obtained was heated to 75° C. to redissolve the solid, filtered, and the filtrate slowly cooled to 5° C. The white crystalline solid thus produced was filtered off, and recrystallized from 525 ml of 5% aqueous acetic acid, to yield pure 9-(2-hydroxyethoxymethyl)guanine (24.8 g, 66.6%). $^1$NMR,: 3.38 (4H, singlet); 4.64 (1H, broad singlet); 5.26 (2H, singlet); 6.54 (2H, broad singlet); 7.68 (1H, singlet).

EXAMPLE 5

Alternative Preparation of a Compound of Formula (I)

A mixture of guanine (25 g), hexamethyldisilazane (HMDS, 135 ml), and trifluoromethanesulfonic acid (0.75 ml) was heated to reflux (130°–135° C.) for 24 hours. The resulting mixture was cooled to 70° C., and excess HMDS removed by distillation (0.1 to 1 mm Hg), slowly raising the bath temperature back to 110° C. The resulting mixture was cooled to 50° C., 1,3-dioxolane (36 ml) added, and the resulting mixture refluxed for 16 hours. The mixture was then cooled to 60° C., 300 ml of water and 2 ml of acetic acid added, and then low boiling solvent was removed by distillation at atmospheric pressure. The reaction mixture was cooled, and the yellow solid filtered off, which was then dissolved in a mixture of 450 ml water and 24 ml of acetic acid at 80° C. The hot solution was treated with a small amount of activated carbon (2 g) to remove any color, filtered, and the filtrate slowly cooled to 5° C., to yield pure 9-(2-hydroxyethoxymethyl)guanine (27.4 g, 73%). $^1$ NMR: 3.38 (4H, singlet); 4.64 (1H, broad singlet); 5.26 (2H, singlet); 6.54 (2H, broad singlet); 7.68 (1H, singlet).

EXAMPLE 6

Alternative Preparation of a Compound of Formula (I)

A mixture of guanine (15.1 g), hexamethyldisilazane (HMDS, 28 ml), and trifluoromethanesulfonic acid (0.45 ml) was heated to reflux for 6 hours. The resulting mixture was cooled to 70° C., and excess HMDS removed by distillation (0.1 to 1 mm Hg), slowly raising the bath temperature back to 100° C. To the residue was added 150 ml of toluene and 1,3-dioxolane (10.5 ml), and the mixture refluxed for 6 hours. The mixture was then cooled and washed with a solution of 4.2 g of sodium hydroxide in 250 ml of water, followed by 50 ml of water. To the aqueous extract was added 22.6 ml of acetic acid and activated carbon, and the mixture heated to 90° C., filtered, and the filtrate cooled to 10° C., to yield pure 9-(2-hydroxyethoxymethyl)guanine (7.9 g). $^1$H NMR 3.38 (4H, singlet); 4.64 (1H, broad singlet); 5.26 (2H, singlet); 6.54 (2H, broad singlet); 7.68 (1H, singlet).

EXAMPLE 7

Alternative Preparation of a Compound of Formula (I)

A mixture of guanine (60 Kg), hexamethyldisilazane (HMDS, 300 liters), and trifluoromethanesulfonic acid (3 Kg) was heated to reflux for 36 hours. The resulting mixture was cooled to 80° C., excess HMDS removed by distillation (35 mm Hg), and toluene (600 liters) and 1,3-dioxolane (41 liters) added. The mixture was refluxed at 105° C. for 8 hours. The mixture was then cooled and filtered. To the filtrate was added a solution of sodium hydroxide (17 Kg) in 600 liters of water, the aqueous (bottom) layer separated. To this aqueous layer was added a further 600 liters of water, and the mixture was made acidic by addition of acetic acid (91 liters). Filtrol (7 Kg) and celatom (3 Kg) was added, and the mixture heated to 40°–60° C. and toluene and excess dioxolane removed under reduced pressure (100 mm), and then heated to 80°–90° C. to dissolve the product. The mixture was filtered to remove the filtrol and celatom, and the filtrate cooled to 20°–30° C. and neutralized to pH 6.5–7 by addition of 95 Kgs of aqueous 50% sodium hydroxide. To this was added ammonium hydroxide (29%, 14 liters), and the mixture was then heated to 80°–90° C. in order to dissolve the solid. The solution was seeded and cooled to 10°–15° C., and the precipitate filtered off, to yield 9-(2-hydroxyethoxymethyl)guanine (59.5 Kg, 67%). This product shows 99% or greater purity.

The product was dissolved in 30 volumes of water at 75°–80° C., 10% w/w decolorizing charcoal (ADP) added, and the mixture filtered hot. The filtrate was seeded and cooled to 10°–15° C., and the crystalline product filtered off and dried under vacuum at 60°–70° C., to yield pure 9-(2-hydroxyethoxymethyl)guanine (53.5 Kg, 60% yield). $^1$ NMR: 3.38 (4H, singlet); 4.64 (1H, broad singlet); 5.26 (2H, singlet); 6.54 (2H, broad singlet); 7.68 (1H, singlet).

EXAMPLE 8

Alternative Preparation of a Compound of Formula (I)

A mixture of guanine (25 g), hexamethyldisilazane (HMDS, 125 ml), and trifluoromethanesulfonic acid (0.75 ml) was heated to reflux (130°–135° C.) for 18 hours. The resulting mixture was cooled to 70° C., and excess HMDS removed by distillation (0.1 to 1 mm Hg). The resulting mixture was cooled, and toluene (250 ml) and 1,3-dioxolane (18 ml) added, and the resulting mixture refluxed for 10 hours at 105° C. The mixture was then cooled and 250 ml of water containing sodium hydroxide (7 g) added, and the aqueous layer separated. The toluene layer was washed with water (150 ml), and the combined aqueous layers were heated at atmospheric pressure to distill off low boiling organic material. The solution was cooled, and acetic acid (10.5 g) added to give a white precipitate. To this was added 29% ammonium hydroxide (6 g), the mixture heated to dissolve the solid, and the hot solution treated with a small amount of activated carbon (3 g) to remove any color. The slurry thus obtained was heated to redissolve the solid, filtered, and the filtrate slowly cooled to 5° C. The white crystalline solid thus produced was filtered off, to yield pure 9-(2-hydroxyethoxymethyl)guanine (26.8 g, 72%) $^1$NMR: 3.38 (4H, singlet); 4.64 (1H, broad singlet); 5.26 (2H, singlet); 6.54 (2H, broad singlet); 7.68 (1H, singlet).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A process for preparing a compound represented by the formula:

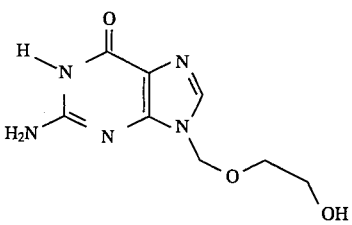

said process comprising:

a) contacting a compound or mixture of compounds represented by Formula (2):

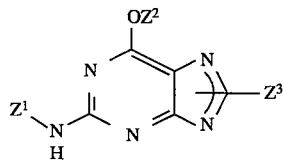

wherein:
  $Z^1$ is hydrogen or $R^1R^2R^3Si$;
  $Z^2$ is hydrogen or $R^1R^2R^3Si$;
  $Z^3$ is hydrogen or $R^1R^2R^3Si$;

in which $R^1$, $R^2$, and $R^3$ are independently lower alkyl; provided that at least one of $Z^1$, $Z^2$ and $Z^3$ is $R^1R^2R^3Si$; with a compound of Formula (3):

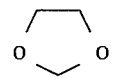

in the presence of a selective alkylation catalyst selected from the group consisting of trifluoromethanesulfonic acid, trimethylsilyl trifluoromethanesulfonate, and bistrimethylsilyl sulfonate, and b) hydrolyzing the product thus formed.

2. A process for preparing a compound represented by the formula:

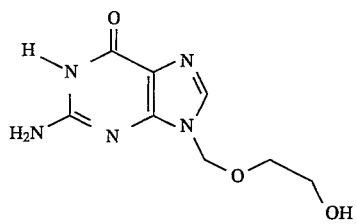

said process comprising:

a) contacting a compound or mixture of compounds represented by Formula (2):

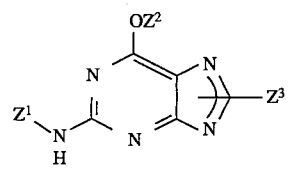

wherein:
  $Z^1$ is hydrogen or $R^1R^2R^3Si$;
  $Z^2$ is hydrogen or $R^1R^2R^3Si$;
  $Z^3$ is hydrogen or $R^1R^2R^3Si$;

in which $R^1$, $R^2$, and $R^3$ are independently lower alkyl; provided that at least one of $Z^1$, $Z^2$ and $Z^3$ is a silyl group; with a compound of Formula (3):

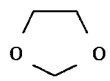

in the presence of a selective alkylation catalyst selected from the group consisting of trifluoromethanesulfonic acid, trimethylsilyl trifluoromethanesulfonate, and bistrimethylsilyl sulfonate, to obtain a compound of Formula (4):

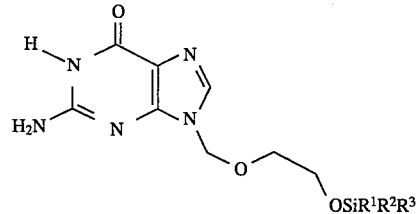

where $R^1$, $R^2$, and $R^3$ are as defined above; followed by b) purifying the compound of Formula (4) by precipitation or crystallization from an inert solvent; and c) hydrolyzing the purified compound of Formula (4).

3. The process of claim 1, wherein said catalyst is trimethylsilyl trifluoromethanesulfonate.

4. The process of claim 3, wherein $R^1$, $R^2$, and $R^3$ are all methyl.

5. The process of claim 4, in which both the compound of Formula (2) and the trimethylsilyl trifluoromethanesulfonate are generated concurrently by contacting guanine with hexamethyldisilazane in the presence of trifluoromethanesulfonic acid.

6. The process of claim 5, wherein the compound of Formula (2) is a compound of the formula:

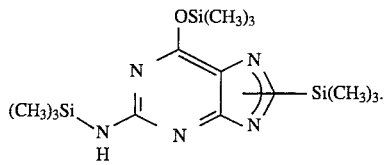

7. The process of claim 6, wherein said hydrolysis is carried out with a mixture of an alkanoic acid and water.

8. The process of claim 7, wherein said alkanoic acid is acetic acid.

9. The process of claim 6, wherein said hydrolysis is carried out with aqueous base.

10. The process of claim 9, wherein said base is sodium hydroxide.

11. A process for preparing a compound represented by the formula:

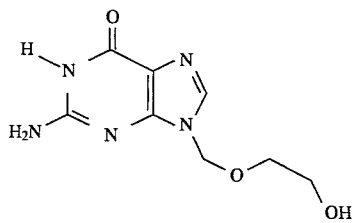

said process comprising:
a) contacting guanine with hexamethyldisilazane in the presence of trifluoromethanesulfonic acid;
b) contacting the mixture thus formed with a compound of Formula (3):

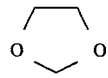 (3)

c) hydrolyzing the product thus formed by treatment with an aqueous base; and d) neutralizing the resultant solution with an acid.

12. The process of claim 11, wherein the base of step c) is sodium hydroxide.

13. The process of claim 2, wherein said catalyst is trimethylsilyl trifluoromethanesulfonate.

14. The process of claim 13, wherein $R^1$, $R^2$, and $R^3$ are all methyl.

15. The process of claim 14, in which both the compound of Formula (2) and the trimethylsilyl trifluoromethanesulfonic are generated concurrently by contacting guanine with hexamethyldisilazane in the presence of trifluoromethanesulfonic acid.

16. The process of claim 15, wherein the compound of Formula (2) is a compound of the formula:

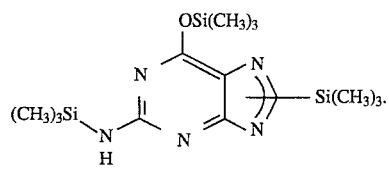

17. The process of claim 16, wherein said inert solvent is a mixture of acetone and water.

18. The process of claim 17, wherein said hydrolysis is carried out with a mixture of an alkanoic acid and water.

19. The process of claim 18, wherein said alkanoic acid is acetic acid.

20. The process of claim 16, wherein said hydrolysis is carried out with aqueous base.

21. The process of claim 20, wherein said base is sodium hydroxide.

22. The process of claim 11, wherein step b) is carried out with toluene as a solvent.

23. The process of claim 11, wherein the acid of step d) is acetic acid.

24. The process of claim 11, wherein the 9-(2-hydroxyethoxymethyl)guanine product of step d) is crystallized from ammonium hydroxide solution.

25. The process of claim 11, wherein the crystalline 9-(2-hydroxyethoxymethyl)guanine product is recrystallized from water.

* * * * *

UNITED STATES PATENT AND TRADEMARK OFFICE
CERTIFICATE OF CORRECTION

PATENT NO. : 5,567,816
DATED : Oct. 22, 1996
INVENTOR(S) : Schloemer et al.

It is certified that error appears in the above-indentified patent and that said Letters Patent is hereby corrected as shown below:

Claim 15, at column 14, line 10 "sulfonic are generated concurrently by contacting guanine" should read -- sulfonate are generated concurrently by contacting guanine --.

Claim 25, column 14, line 41 "The process of claim 11, wherein the crystalline" should read -- The process of claim 24, wherein the crystalline --.

Signed and Sealed this

Fourth Day of February, 1997

*Attest:*

BRUCE LEHMAN

*Attesting Officer*   *Commissioner of Patents and Trademarks*